(12) United States Patent
Braden

(10) Patent No.: US 11,654,249 B2
(45) Date of Patent: May 23, 2023

(54) NEEDLE RETENTION AND DISPOSAL DEVICE

(71) Applicant: Arkansas Children's, Inc., Little Rock, AR (US)

(72) Inventor: Eric D. Braden, Little Rock, AR (US)

(73) Assignee: Arkansas Children's, Inc., Little Rock, AR (US)

( * ) Notice: Subject to any disclaimer, the term of this patent is extended or adjusted under 35 U.S.C. 154(b) by 187 days.

(21) Appl. No.: 17/146,741

(22) Filed: Jan. 12, 2021

(65) Prior Publication Data

US 2021/0220566 A1 Jul. 22, 2021

Related U.S. Application Data

(60) Provisional application No. 62/961,807, filed on Jan. 16, 2020.

(51) Int. Cl.
*A61M 5/32* (2006.01)
*B65D 83/00* (2006.01)

(52) U.S. Cl.
CPC ....... *A61M 5/3205* (2013.01); *B65D 83/0005* (2013.01); *B65D 83/0038* (2013.01)

(58) Field of Classification Search
CPC ............. A61M 5/3205; B65D 83/0005; B65D 83/0038
See application file for complete search history.

(56) References Cited

U.S. PATENT DOCUMENTS

| | | | |
|---|---|---|---|
| 4,576,281 A * | 3/1986 | Kirksey | A61M 5/3205 206/370 |
| 4,746,008 A | 5/1988 | Heverly | |
| 4,969,554 A * | 11/1990 | Sawaya | A61B 50/362 229/128 |
| 5,020,665 A | 6/1991 | Bruno | |
| 5,076,429 A | 12/1991 | Patrick | |
| 5,145,063 A | 9/1992 | Lee | |

(Continued)

FOREIGN PATENT DOCUMENTS

ES 147634 7/1969

OTHER PUBLICATIONS

Covidien 89671 Multi-Purpose Sharps Containers with Horizontal-Drop Opening Lid, 2 gal Capacity, 12.75" Height×7.25" Depth×10.5" Width, Transparent Red (Pack of 20), https://www.amazon.com/89671-Multi-Purpose-Containers-Horizontal-Drop-Transparent/dp/B01BQA8ROQ8 (last accessed Dec. 18, 2020).

(Continued)

*Primary Examiner* — Michael Collins
(74) *Attorney, Agent, or Firm* — Richard Blakely Glasgow

(57) ABSTRACT

A needle retention and disposal device including a cup having an interior compartment for receiving and retaining used needles and a skirt having a bottom open end. The cup is positioned inside the skirt and is springedly attached to the skirt. Two doors are rotatably attached to the interior compartment of the cup and are moveable between an open position and a closed position. The bottom open end of the skirt receives the neck of a sharps container such that the neck of the sharps container contacts the bottom surface of the cup. The doors are moveable from the closed position to the open position to release the used needles when the skirt is pushed down over the neck of the sharps container.

13 Claims, 15 Drawing Sheets

(56) References Cited

U.S. PATENT DOCUMENTS

| | | | | |
|---|---|---|---|---|
| 5,201,418 | A | * | 4/1993 | Hanlon ................ A61M 5/3205 220/908 |
| 5,245,117 | A | * | 9/1993 | Withers ................ A61M 5/002 405/129.55 |
| 5,603,404 | A | | 2/1997 | Nazare |
| 6,036,671 | A | * | 3/2000 | Frey .................... A61M 5/3205 604/110 |
| 7,392,903 | B2 | | 7/2008 | Jolley |
| 7,556,149 | B2 | * | 7/2009 | Erickson ............... A61M 5/002 206/365 |
| 7,891,487 | B2 | | 2/2011 | Erickson |
| 8,083,098 | B1 | * | 12/2011 | Schaffer ................ A61M 5/002 221/226 |
| 10,321,968 | B2 | | 6/2019 | Burgess |
| 2005/0236289 | A1 | * | 10/2005 | Tanaka ................ A61M 5/3205 206/370 |
| 2009/0114667 | A1 | * | 5/2009 | Sansoucy ............ A61B 50/362 221/34 |
| 2021/0170092 | A1 | * | 6/2021 | Zhou ................... A61M 5/008 |

OTHER PUBLICATIONS

5-Quart Biohazard Patient Room Sharps Container | MedLine MDS705153, https://www.vitalitymedical.com/medline-mds705153-5-quart-biohazard-patient-room-sharps-container-red-clear.html (last accessed Dec. 18, 2020).

Dynarex 2 Quart Medical Grade Sharps Needle Container, Red, DYX-4623, https://www.walmart.com/ip/Dynarex-2-Ouart-Medical-Grade-Sharps-Needle-Container-RED-DYX-4623/46087021 (last accessed Dec. 18, 2020).

Kendal 8900SA Sharps Container 1 Quart, Red, https://fsastore.com/Kendal-8900SA-Sharps-Container-1-Quart-Red-P18432.aspx utm_source=google&utm_id=go_cmp-649052389_adg-91413211650_ad-420364249182_pla-877414557507_dev-c_ext-_prd-18432_sig-EAIaIQobChMlwPWqnceF7AIVJRvnCh0nNQ3PEAQYAyABEglvt_D_BwE&gclid=EAIaIQobChMlwPWqnceF7AIVJRvnCh0nNQ3PEAQYAyABEglvt_D_BwE (last accessed Dec. 18, 2020).

Dakridge 5 Quart—Sharps Disposal Container with Mailbox Style Lid, https://www.amazon.com/Oakridge-Quart-Disposal-Container-Mailbox/dp/B00KQXAXBC (last accessed Dec. 18, 2020).

* cited by examiner

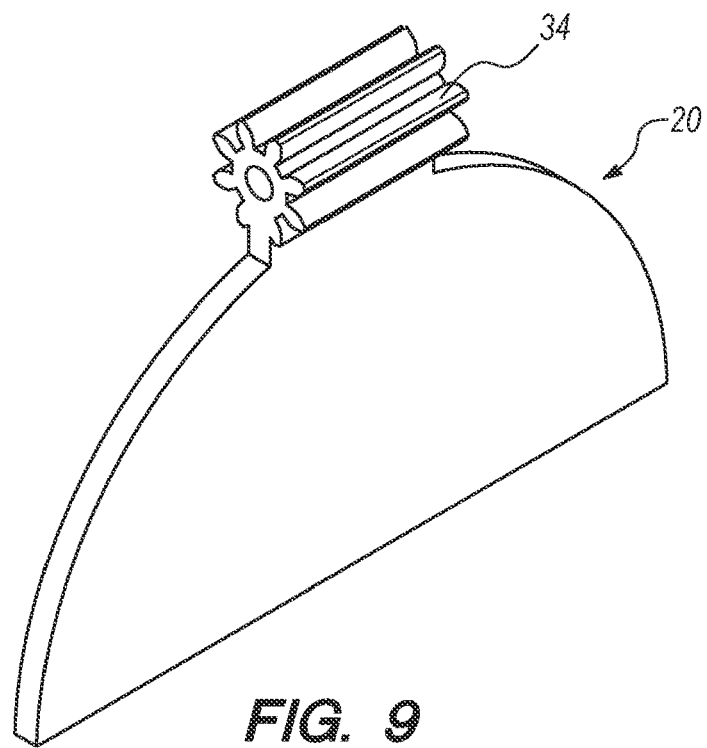
FIG. 9
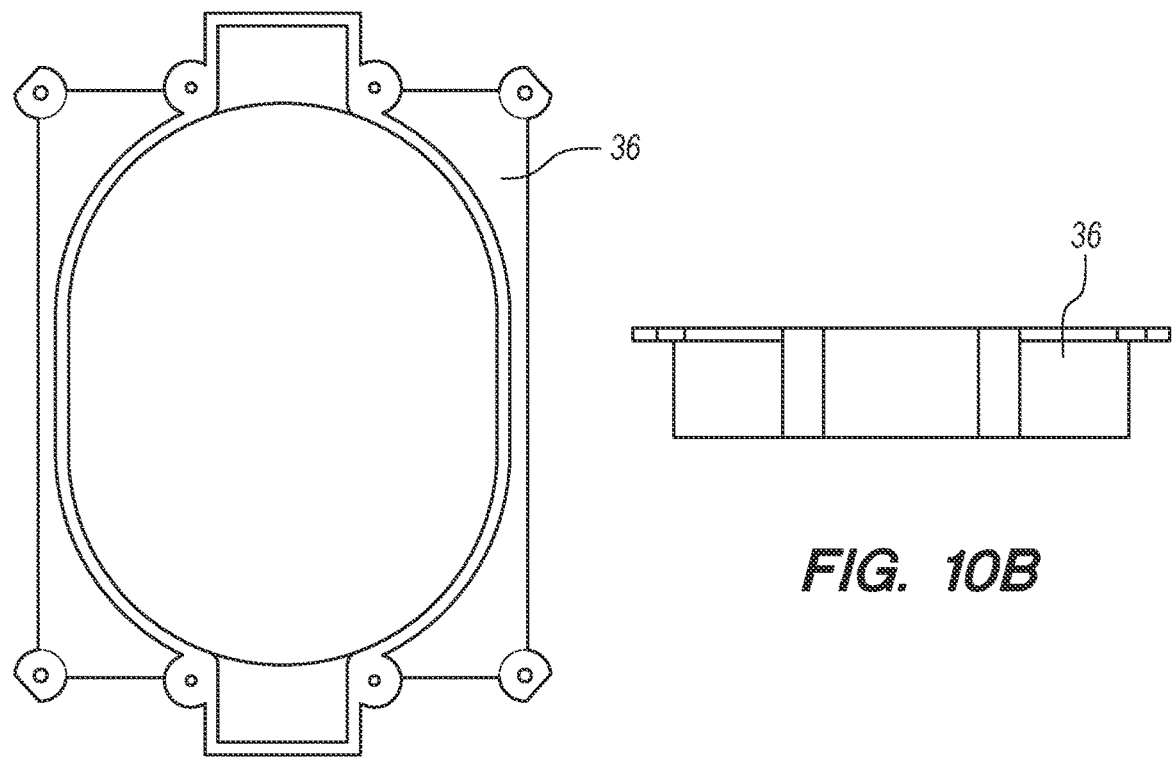
FIG. 10A
FIG. 10B

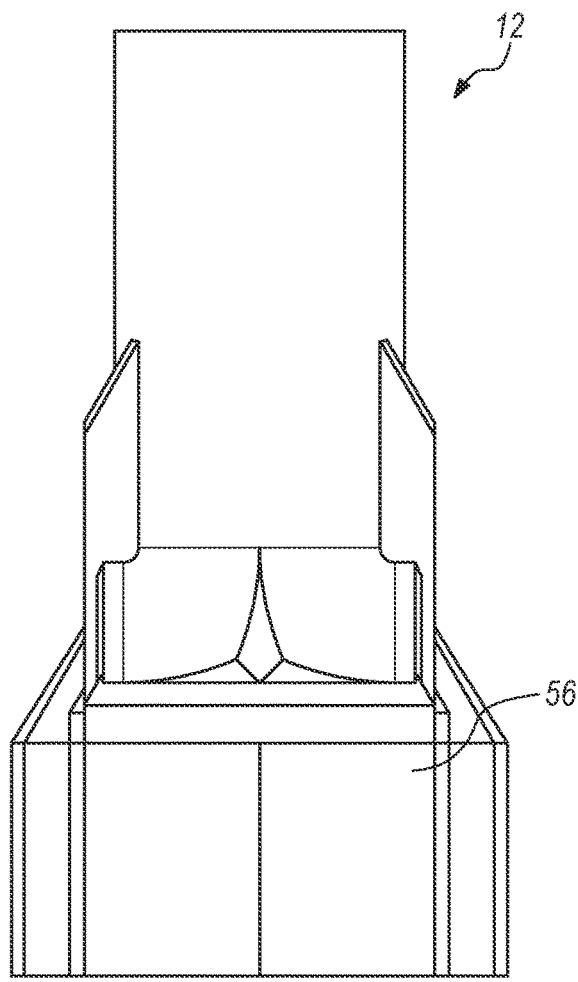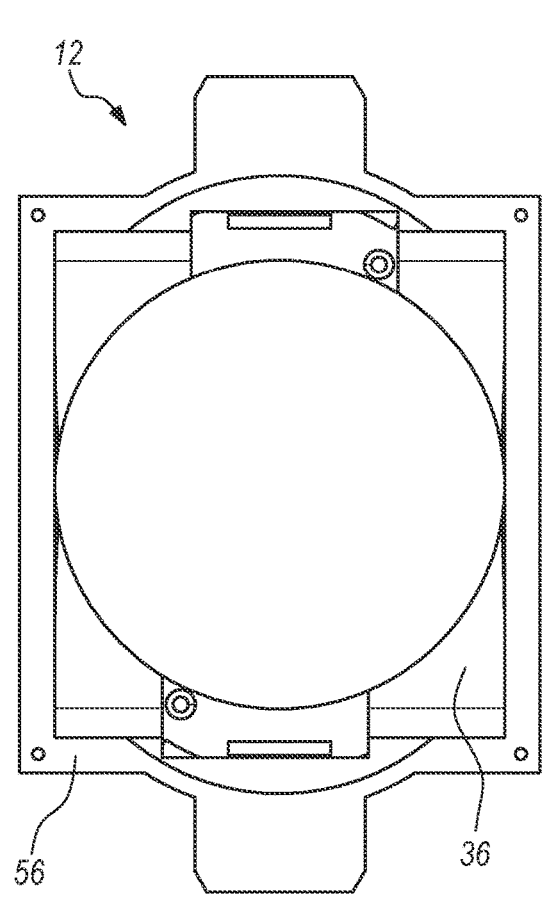
FIG. 23
FIG. 24

NEEDLE RETENTION AND DISPOSAL DEVICE

CROSS-REFERENCE TO RELATED APPLICATIONS

This application claims the benefit of U.S. Provisional Application No. 62/961,807, filed on Jan. 16, 2020, and entitled "Needle Retention and Disposal Device." Such application is incorporated herein by reference in its entirety.

STATEMENT REGARDING FEDERALLY SPONSORED RESEARCH OR DEVELOPMENT

Not applicable

BACKGROUND OF THE INVENTION

The present invention is directed to the problem of unintended needle sticks to medical professionals (e.g., nurses) in medical facilities. Nurses do not have a safe and effective way to dispose of needles immediately after giving shots. Although safety devices that close and cover the needles are used, they sometimes fail. Additionally, direct disposal sharps containers are not placed within arm's length of the medical professionals. As a result, nurses commonly place the needles on the bed or on a tray until they are able to release the patient and turn around to place them in the sharps container. It would therefore be desirable to develop a temporary repository for needles.

BRIEF SUMMARY OF THE INVENTION

The present invention is directed to a needle retention and disposal device that includes a cup having an interior compartment for receiving and retaining used needles and a skirt having a bottom open end. The cup is positioned inside the skirt and is springedly attached to the skirt. Two doors are rotatably attached to the interior compartment of the cup and are moveable between an open position and a closed position. The bottom open end of the skirt is configured to receive the neck of a sharps container such that the neck of the sharps container contacts the bottom surface of the cup. The doors are configured to move from the closed position to the open position to release the used needles from the cup when the skirt is pushed down over the neck of the sharps container.

These and other features, objects and advantages of the present invention will become better understood from a consideration of the following detailed description of the preferred embodiments in conjunction with the drawings as described following:

BRIEF DESCRIPTION OF THE DRAWINGS

FIG. 9 is a perspective view of the door of a preferred embodiment of the needle retention and disposal device.

FIG. 10A is a top view of the cup retainer of a first preferred embodiment of the needle retention and disposal device. FIG. 10B is a side view of the cup retainer of a first preferred embodiment of the needle retention and disposal device.

FIG. 23 is a side perspective view of the skirt of a second preferred embodiment of the needle retention and disposal device.

FIG. 24 is a bottom view of the skirt of a second preferred embodiment of the needle retention and disposal device.

DETAILED DESCRIPTION OF THE INVENTION

With reference to FIGS. 1-28, the preferred embodiments of the needle retention and disposal device of the present invention may be described.

Figure 7:
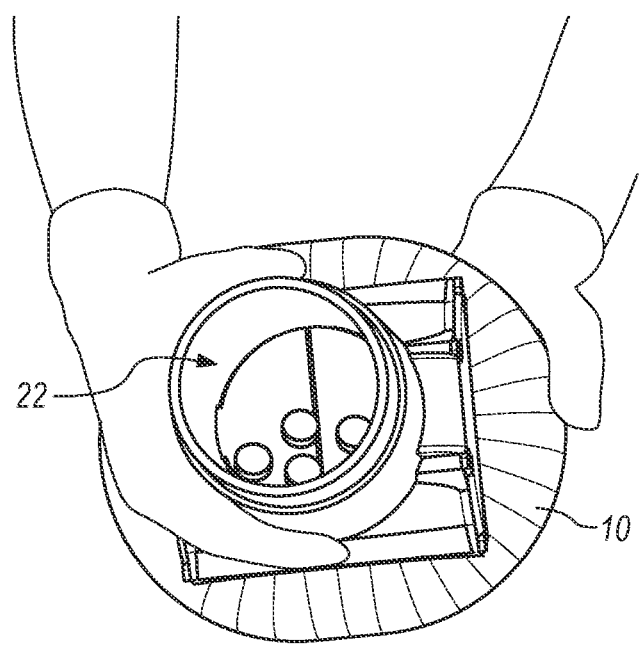
FIG. 7 is a top view of a first preferred embodiment of the needle retention and disposal device being held by a medical professional with needles inside the cup of the device.
Figure 8:
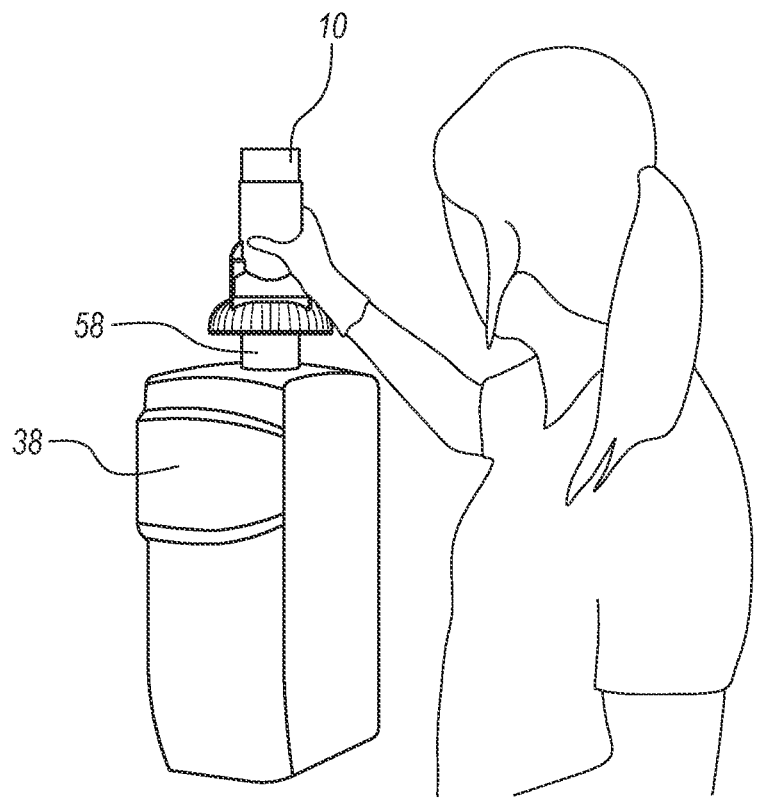
FIG. 8 is a perspective view of a first preferred embodiment of the needle retention and disposal device positioned on top of the neck of a sharps disposal container by a medical professional.
Figure 11A:
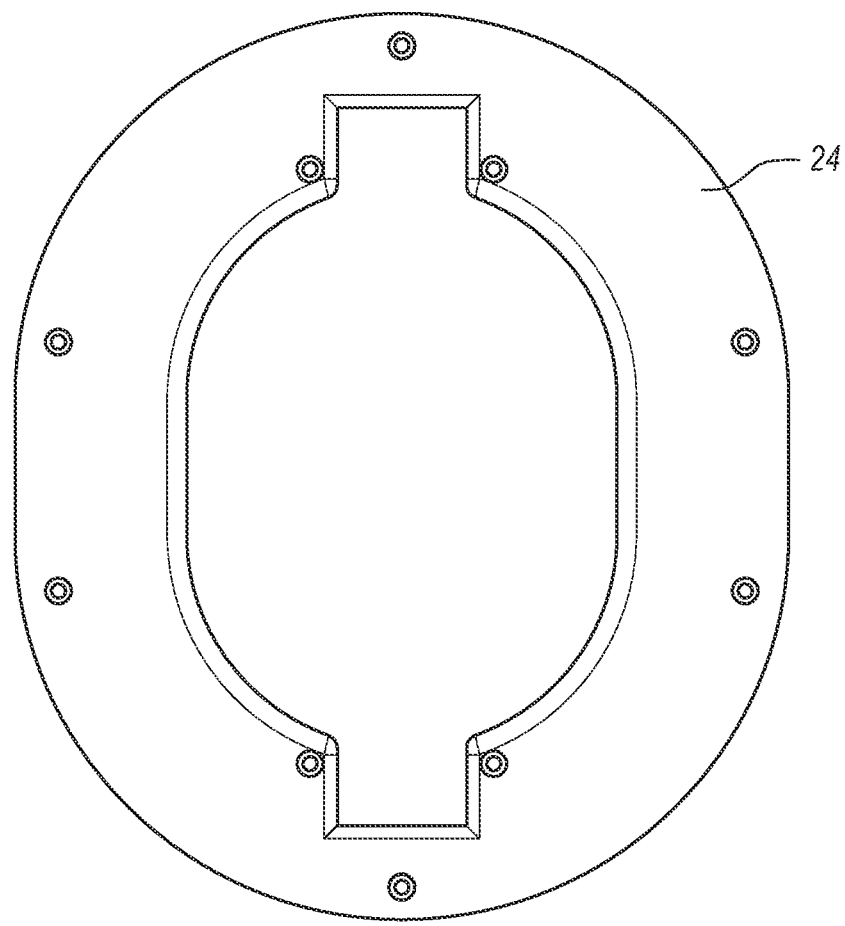
FIG. 11A is a top view of the skirt cap of a first preferred embodiment of the needle retention and disposal device.
Figure 11B:
FIG. 11B is a side view of the skirt cap of a first preferred embodiment of the needle retention and disposal device.
Figure 12:
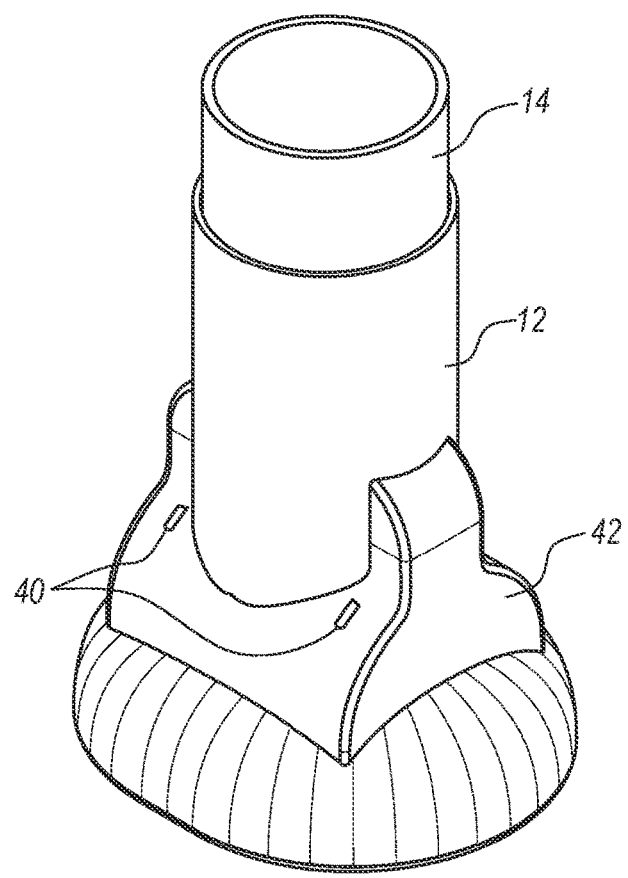
FIG. 12 is a side perspective view of a first preferred embodiment of the needle retention and disposal device.
Figure 13:
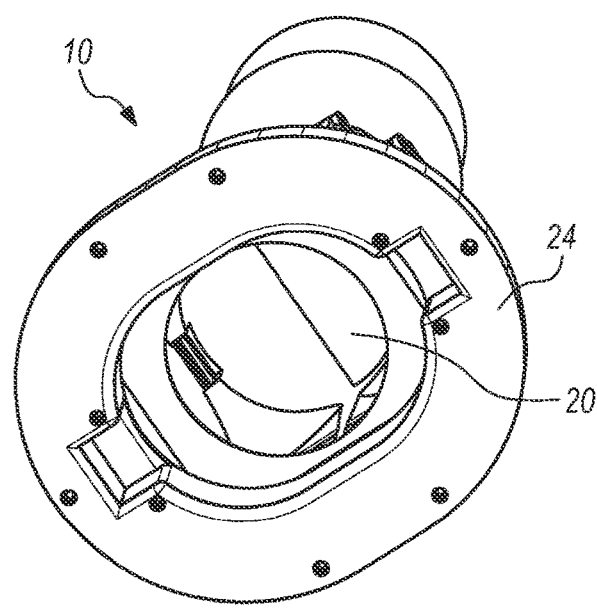
FIG. 13 is a bottom perspective view of a first preferred embodiment of the needle retention and disposal device.
Figure 14:
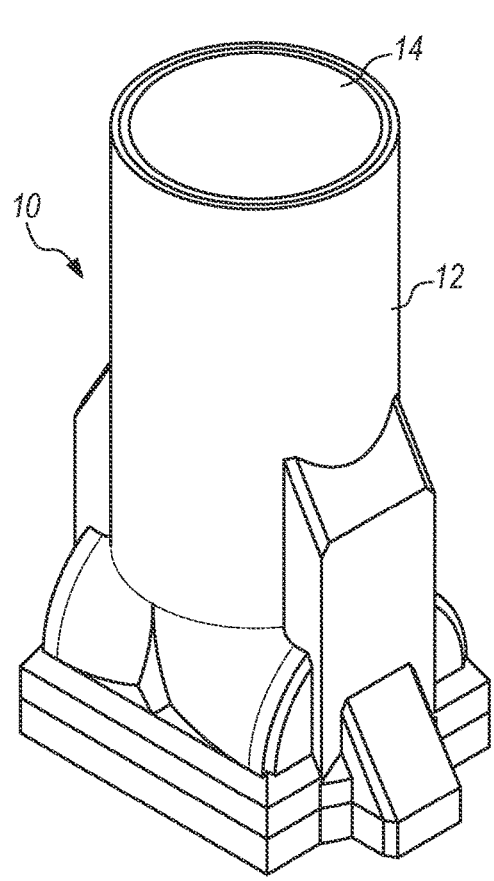
FIG. 14 is a side perspective view of a second preferred embodiment of the needle retention and disposal device.
Figure 15:
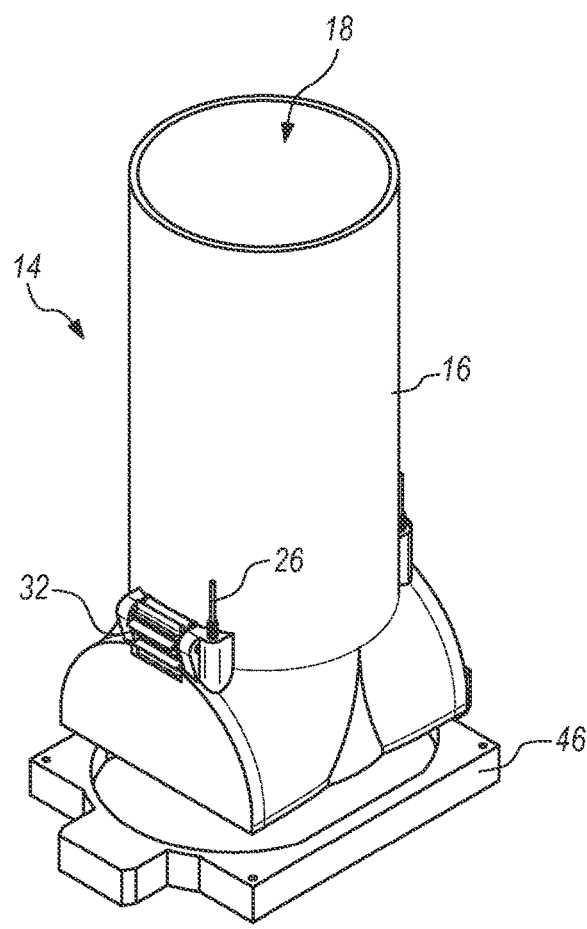
FIG. 15 is a side exploded view of the cup and the base of a second preferred embodiment of the needle retention and disposal device.
Figure 16:
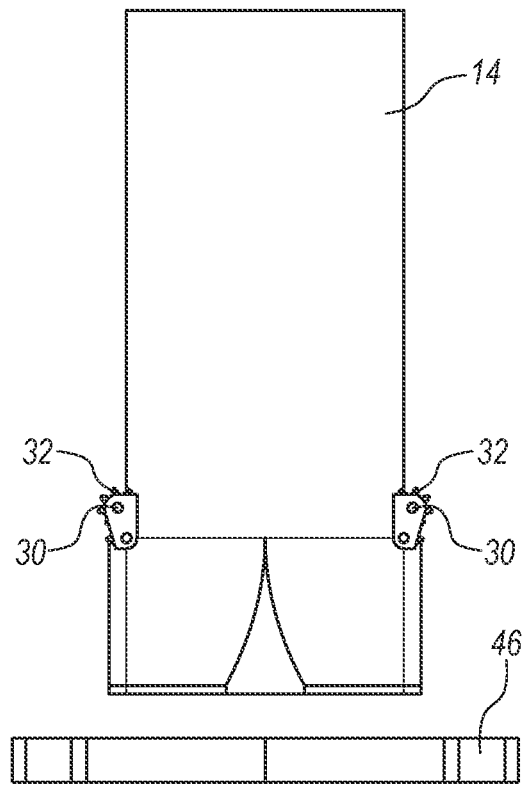
FIG. 16 is a front exploded view of the cup and the base of a second preferred embodiment of the needle retention and disposal device.

The needle retention and disposal device 10 acts as a temporary repository for sharps. After a shot is administered, the needle is dropped into the device. As shown in FIGS. 7-8, once all of the used needles have been placed in the device 10, the medical professional places the device 10 over a sharps disposal container 38 and presses downward on the device. This action causes the needles in the device to be dropped into the more permanent sharps container.

Figure 1:
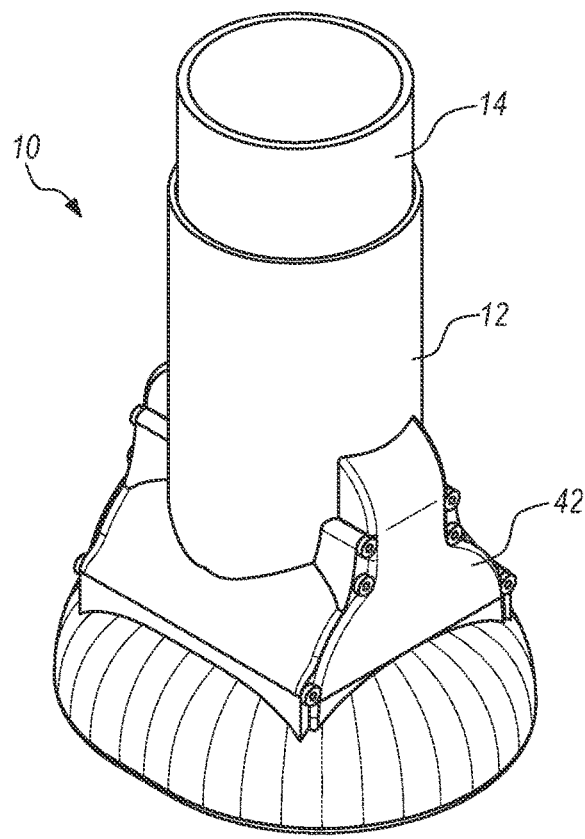
FIG. 1 is a side perspective view of a first preferred embodiment of the needle retention and disposal device.
Figure 2:
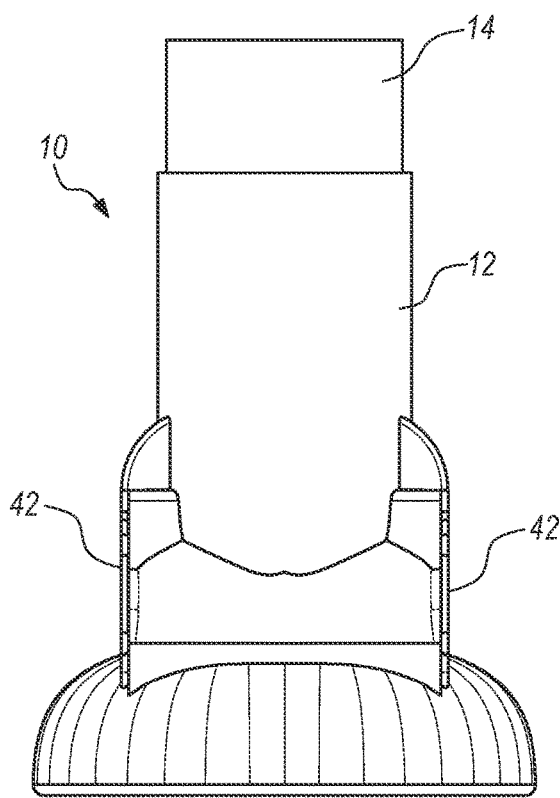
FIG. 2 is a front perspective view of a first preferred embodiment of the needle retention and disposal device.
Figure 5:
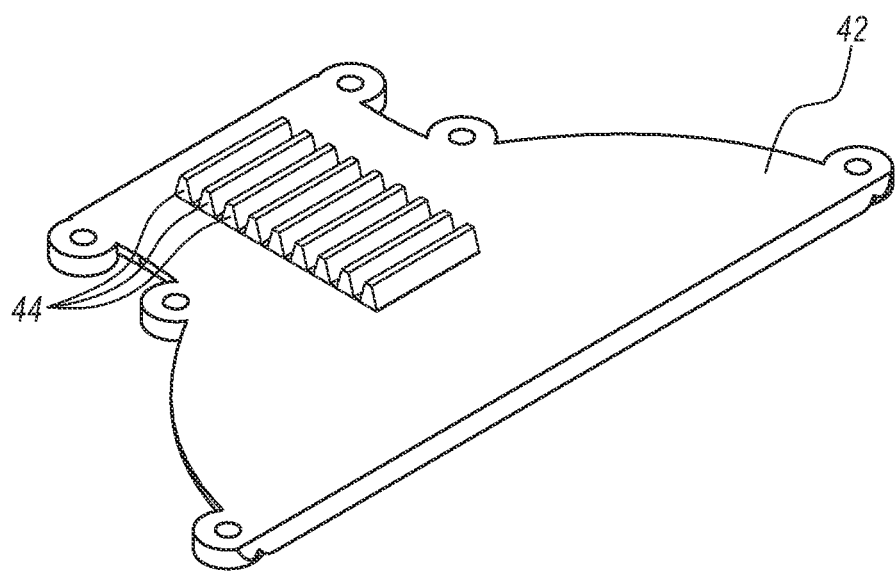
FIG. 5 is a top view of the inner surface of the skirt panel of a first preferred embodiment of the needle retention and disposal device.
Figure 6:
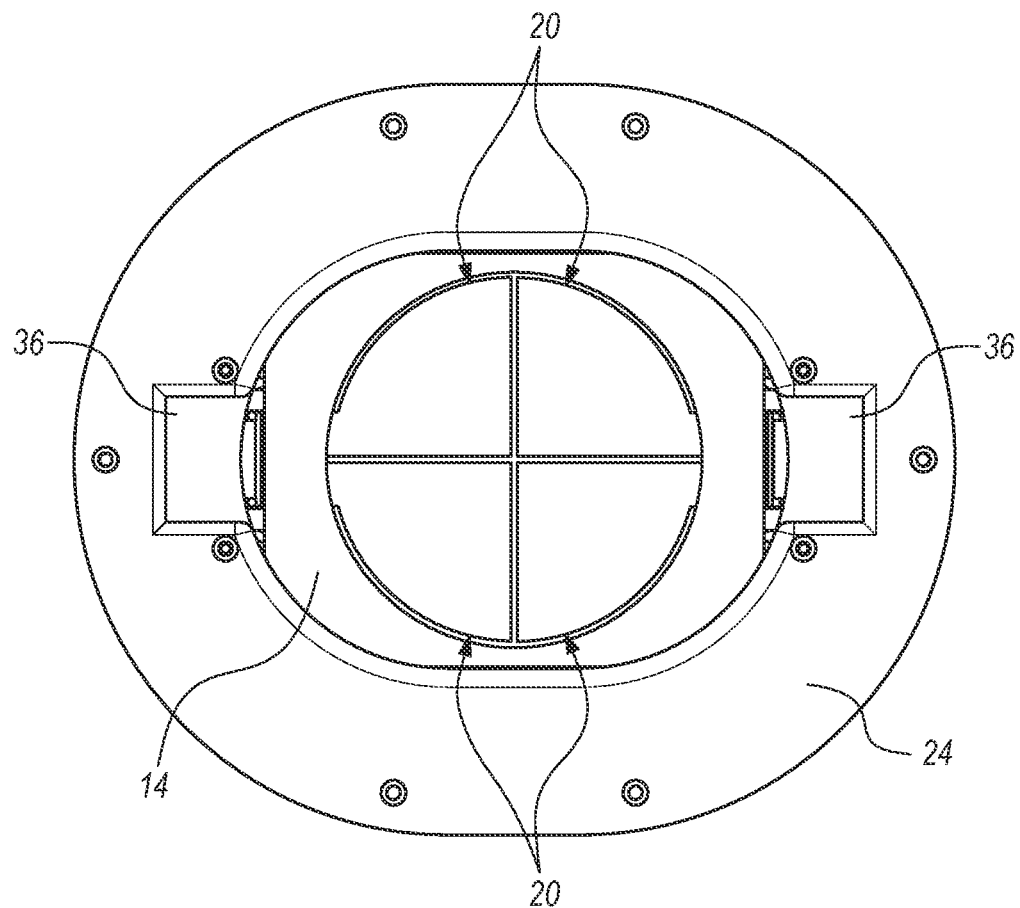
FIG. 6 is a bottom view of a first preferred embodiment of the needle retention and disposal device.

The first embodiment of the needle retention and disposal device 10 is illustrated in FIGS. 1-13. As shown in FIGS. 1-2 and 6, the exterior of the needle retention and disposal device 10 includes a skirt 12, a cup 14, a skirt cap 24, and two skirt panels 42. The skirt 12 covers and protects the internal moving parts and provides an easily cleanable exterior surface. The skirt has a hollow interior with a top opening and a bottom opening. The interior of the skirt 12 receives the cup 14, as shown in FIGS. 1-2. The cup 14 includes a cylinder 16 with an opening 18 and a set of doors 20 closing the opposite end of the cylinder 16. The medical professional may place the used needles through the opening 18 and into the interior compartment 22 of the cup 14. When the doors 20 are closed, the used needles are held in the interior compartment 22 of the cup. Conversely, when the doors 20 are opened, the used sharps are released from the interior compartment 22 of the cup and dropped out of the device 10.

Figure 3A:
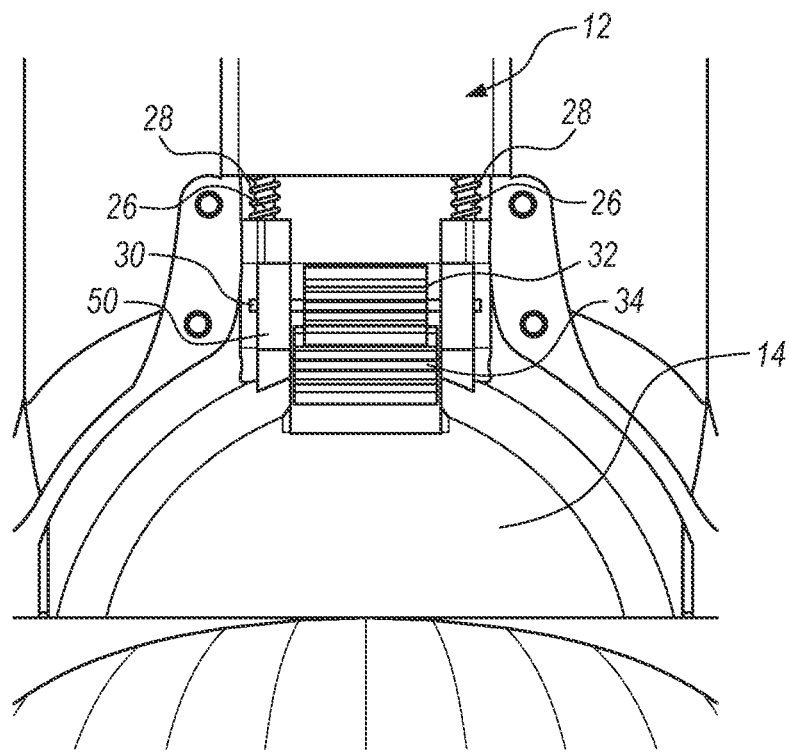
FIG. 3A is a side perspective view of a first preferred embodiment of the needle retention and disposal device with the skirt panel removed.
Figure 3B:
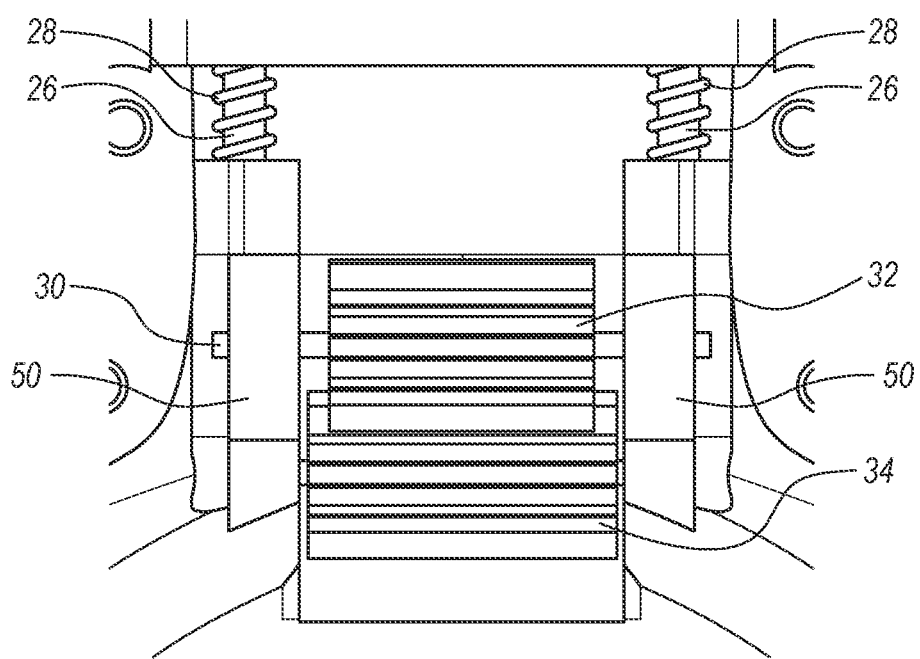
FIG. 3B is a close-up side perspective view of a first preferred embodiment of the needle retention and disposal device with the skirt panel removed.

As shown in FIGS. 3A-3B, the cup 14 is attached to the skirt 12 via four pins 26. Two of the pins 26 are positioned on one side of the skirt 12 and the other two pins 26 are positioned on the opposite side of the skirt 12. For each pin 26, the top end of the pin 26 is attached to the skirt 12, while the bottom end of the pin 26 is attached to the cup 14. The bottom end of the pin 26 is preferably attached to the cup directly above the doors 20. Each pin is received through the center of a compression spring 28. The pins 26 and springs 28 allow the skirt 12 to move up-and-down relative to the cup 14.

Two horizontally-oriented pins 30 are attached to the exterior of the cup 14 and each receives a gear 32 comprising a plurality of teeth, as shown in FIGS. 3A-3B. The pins 30 are attached on opposite sides of the cup 14. In one embodiment, pin covers 40 are attached to the skirt and cover the ends of the pins 30. The gears 32 rotate on the pins 30. Each door 20 includes a gear portion 34 on one end of the door 20, as shown in FIG. 9. The teeth of the gears 32 attached to the pins 30 engage with the recesses of the gear portion 34 of the doors 20. As shown in FIGS. 1-2 and 5, two skirt panels 42 are attached to the exterior surface of the skirt 12 on opposite sides of the skirt 12. A series of teeth 44 line a portion of the inner surface of the skirt panels. The teeth on the skirt panels 42 engage the recesses of the gears 32.

Figure 4A:
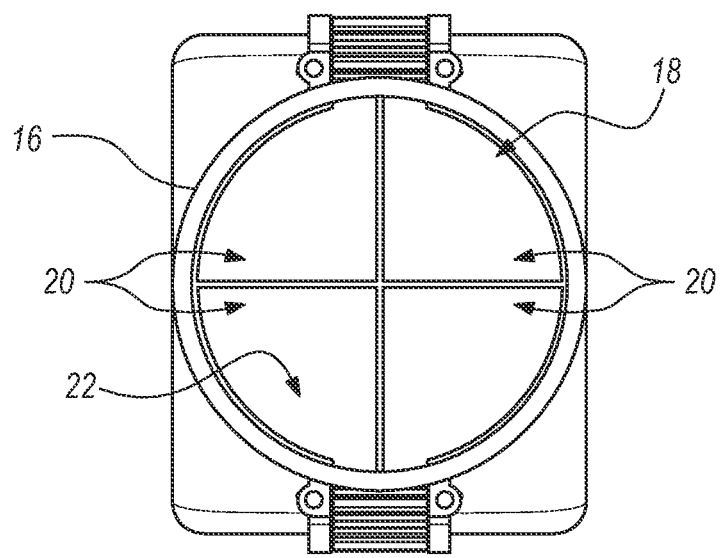
FIG. 4A is a top view of a first preferred embodiment of the needle retention and disposal device with the doors in the closed position.
Figure 4B:
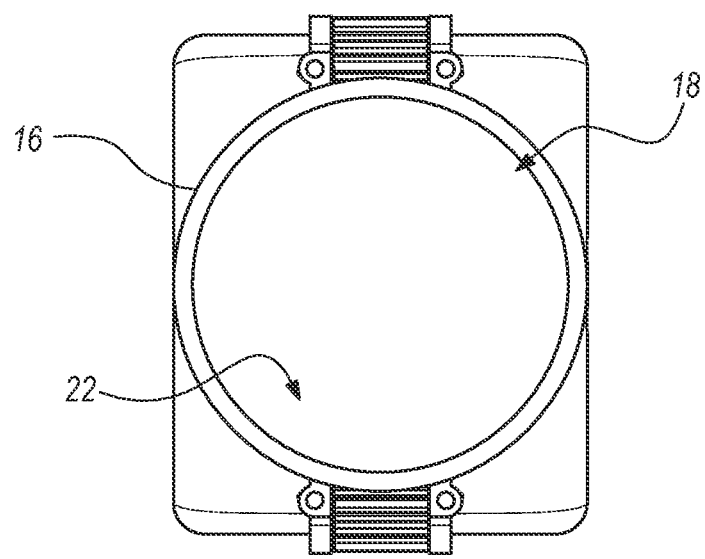
FIG. 4B is a top view of a first preferred embodiment of the needle retention and disposal device with the doors in the open position.

The rotation of the gears 32 in a first direction causes the rotation of the gear portion of the doors 20 in the opposite direction (also referred to as a second direction). The rotation of the gear portion of the doors 20 in the second direction causes the doors to open by rotating downward inside the cup 14. The doors opening allows the contents held inside the cup 14 to be dropped out of the cup. In this embodiment, as shown in FIGS. 4A and 6, the device includes four doors, each covering approximately 25% of the interior of the cup 14. In another embodiment, as described below, the device includes two doors, each covering approximately 50% of the interior of the cup 14. Conversely, rotation of the gears 32 in the second direction causes rotation of the gear portion 34 of the doors 20 in the first direction. This rotation of the gear portion 34 of the doors 20 in the first direction causes the doors to close by rotating upward inside the cup 14.

As shown in FIGS. 6 and 10A-10B, the needle retention and disposal device 10 of the first embodiment also includes a cup retainer 36 that is screwed into the skirt 12. The cup retainer 36 preferably includes an oval-shaped opening with a lip. In one embodiment, the cup retainer 36 may include a rectangular-shaped perimeter with the oval-shaped opening. An alternative embodiment of the cup retainer with an alternative perimeter shape is shown in FIG. 10A-10B. The cup retainer 36 holds the cup 14 in the correct position when the cup 14 is in the resting position (i.e., the doors 20 are in the closed position). In other words, the cup 14 rests against the cup retainer 36, as shown in FIG. 6. The device 10 also includes a skirt cap (or base) 24 that is attached to the bottom of the skirt 12. The skirt cap may be glued to the bottom of the skirt 12 or screwed to the bottom of the skirt 12. In one embodiment, the skirt cap 24 is an oval ring. In an alternative embodiment shown in FIG. 11A, the skirt cap 24 has an alternative inner shape. Steel BBs or other weighted materials are contained in the space between the skirt cap or base and the skirt 12. The skirt cap 24 prevents the steel BBs or other weighted materials from exiting this space. The weighted bottom prevents tipping or sliding of the device. The skirt cap 24 and the steel BBs or other weighted materials may be omitted from the device 10 entirely when a weighted bottom is not needed.

After the needle retention and disposal device is full of used needles, the medical professional places the bottom of the device 10 on the top of the sharps disposal container 38 in the patient or examination room. Thus, the neck 58 of the sharps disposal container 38 is positioned inside the open bottom of the device 10. Then, holding the skirt 12 of the device 10, the medical professional pushes the device 10 down on the neck of the sharps disposal container. The neck 58 of the sharps disposal container 38 contacts the bottom of the cup 14. When this happens, the cup 14 remains essentially stationary, but the skirt 12 continues to move downward over the neck 58 of the sharps disposal container 38. As the skirt moves downward, the springs 28 on the pins 26 are compressed.

As the skirt moves downward, the skirt panel 42 attached to the skirt 12 also moves downward. Because of their engagement with the recesses of the gears 32, the downward movement of teeth of the skirt panel causes rotation of the gears 32 in the first direction. The rotation of the gears 32 in the first direction causes rotation of the gear portion 34 of the door 20 in the second direction. This causes the doors 20 to open by rotating downward inside the cup 14. The doors opening allows the needles to be dropped out of the cup and into the sharps disposal container 38.

Once the needles inside the needle retention and disposal device 10 have been dropped into the sharps disposal container 38, the medical professional releases the downward pressure on the device 10. As a result, the springs 28 decompress, the skirt panel 42 attached to skirt 12 moves upward, the gears are rotated in the second direction, the gear portion 34 of the doors are rotated in the first direction, and the doors are rotated upwardly to close the cup 14.

Figure 17:
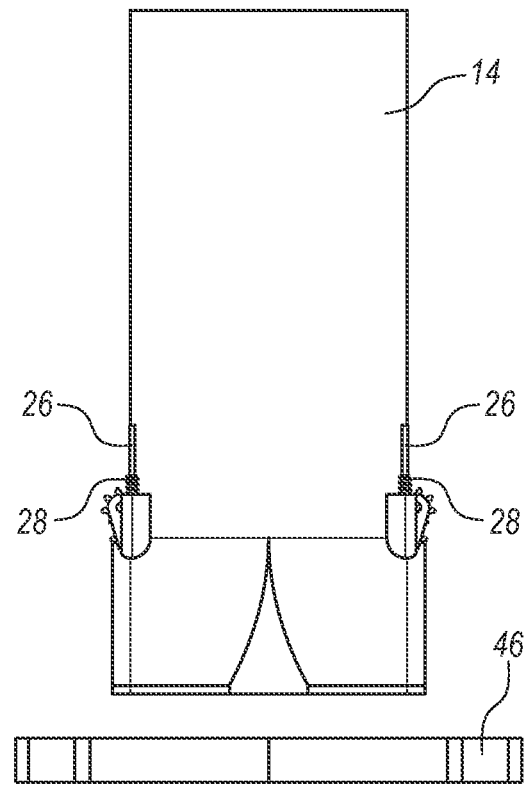
FIG. 17 is a front exploded view of the cup and the base of a second preferred embodiment of the needle retention and disposal device.
Figure 26:
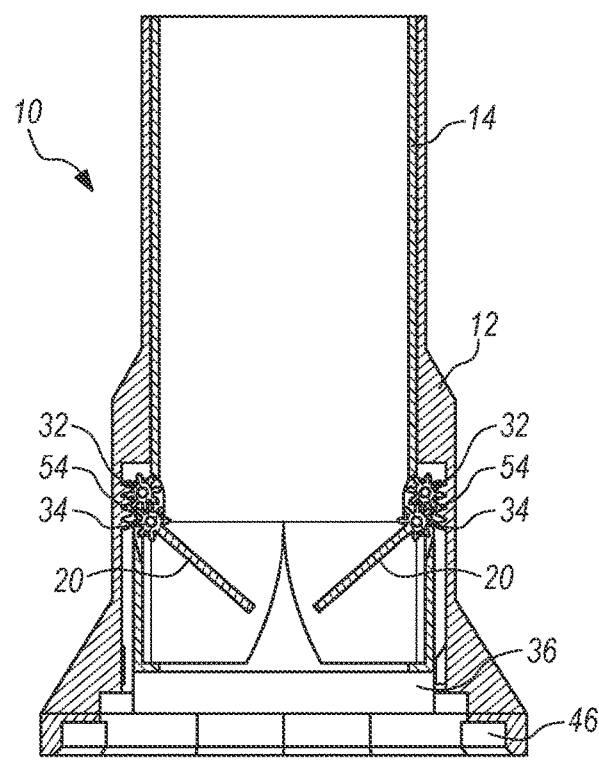
FIG. 26 is a cross-sectional view of a second preferred embodiment of the needle retention and disposal device.
Figure 27:
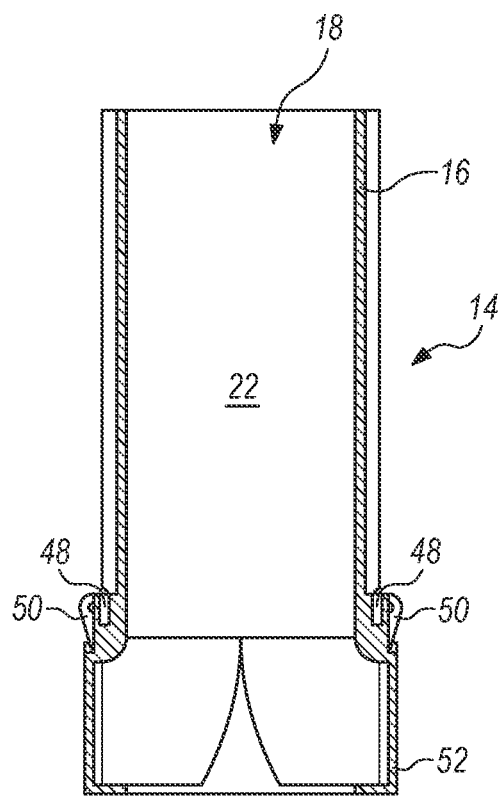
FIG. 27 is a cross-sectional view of the cup of a second preferred embodiment of the needle retention and disposal device.

The second embodiment of the needle retention and disposal device 10 is illustrated in FIGS. 14-28. In this embodiment, the cup 14 is attached to the skirt 12 via two pins 26 instead of four pins. One of the pins 26 is positioned on one side of the cup 14 and the other pin 26 is positioned on the opposite side of the cup 14, as shown in FIG. 17. The bottom end of the pin 26 is inserted into a slot 48 in the cup 14, as shown in FIG. 27, while the top end of the pin 26 is received by the skirt 12. The bottom end of the pin 26 is preferably attached to the cup directly above the doors 20. Each pin is received through the center of a compression spring 28, as shown in FIG. 17. The pins 26 and springs 28 allow the skirt 12 to move up-and-down relative to the cup 14.

Figure 18:
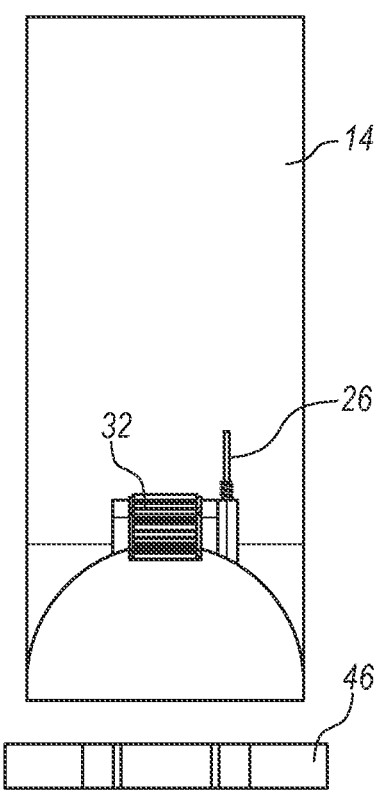
FIG. 18 is a side exploded view of the cup and the base of a second preferred embodiment of the needle retention and disposal device.
Figure 28:
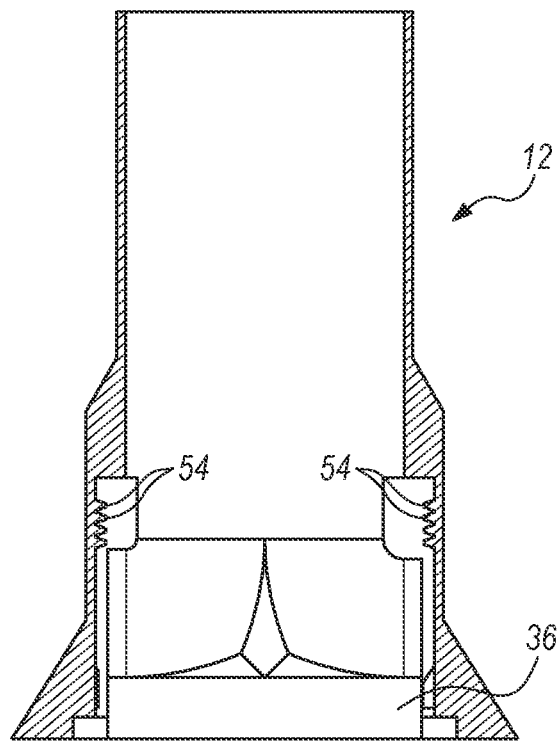
FIG. 28 is a cross-sectional view of the skirt of a second preferred embodiment of the needle retention and disposal device.

Two horizontally-oriented pins 30 are attached between brackets 50 attached to the exterior of the cup 14, as shown in FIG. 27. Each pin 30 receives a gear 32 comprising a plurality of teeth, as shown in FIGS. 18 and 26. The pins 30 are attached on opposite sides of the cup 14. The gears 32 rotate on the pins 30. Each door 20 includes a gear portion 34 on one end of the door 20. The teeth of the gears 32 attached to the pins 30 engage with the recesses of the gear portion 34 of the doors 20, as shown in FIG. 26. This embodiment does not include a skirt panel with teeth. Instead, a series of teeth 54 line a portion of the inner surface of the skirt 12, as shown in FIG. 28. The teeth 54 on the skirt 12 engage the recesses of the gears 32, as shown in FIG. 26.

Figure 19:
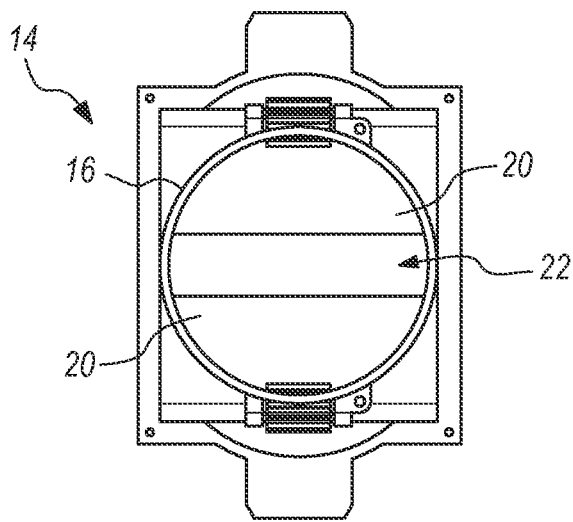
FIG. 19 is a top view of the cup of a second preferred embodiment of the needle retention and disposal device.

The rotation of the gears 32 in a first direction causes rotation of the gear portion of the doors 20 in an opposite direction (also referred to as a second direction). The rotation of the gear portion of the doors 20 in the second direction causes the doors to open by rotating downward inside the cup 14. The doors opening allows the contents held inside the cup 14 to be dropped out of the cup. In this embodiment, the device includes two doors, each covering approximately 50% of the interior of the cup 14, as shown in FIG. 19. Conversely, rotation of the gears 32 in the second direction causes the rotation of the gear portion 34 of the doors 20 in the first direction. This rotation of the gear portion 34 of the doors 20 in the first direction causes the doors to close by rotating upward inside the cup 14.

In the second embodiment, the cup retainer 36 preferably is integral with the skirt 12. The cup retainer 36 preferably includes an oval-shaped opening with a lip. From a top view, the cup retainer 36 may include a rectangular-shaped perimeter with the oval-shaped opening. The cup retainer 36 holds the cup 14 in the correct position when the cup 14 is in the resting position (i.e., the doors 20 are in the closed position). In other words, the base (or bottom) 52 of the cup 14 rests against the cup retainer 36.

After the needle retention and disposal device is full of used needles, the medical professional places the bottom of the device 10 on the top of the sharps disposal container 38 in the patient or examination room. Thus, the neck 58 of the sharps disposal container is positioned inside the open bottom of the device 10. Then, holding the skirt 12 of the device 10, the medical professional pushes the device 10 down on the neck 58 of the sharps disposal container 38. The neck 58 of the sharps disposal container contacts the bottom of the cup. When this happens, the cup 14 remains essentially stationary, but the skirt 12 continues to move downward over the neck 58 of the sharps disposal container. As the skirt moves downward, the springs 28 on the pins 26 are compressed.

As the skirt 12 moves downward, the teeth 44 on the inner surface of the skirt 12 also move downward. Because of their engagement with the recesses of the gears 32, the downward movement of teeth of the skirt causes rotation of the gears 32 in the first direction. The rotation of the gears 32 in the first direction causes the rotation of the gear portion 34 of the door 20 in the second direction. This causes the doors 20 to open by rotating downward inside the cup 14. The doors opening allows the needles to be dropped out of the cup and into the sharps disposal container 38.

Once the needles inside the needle retention and disposal device 10 have been dropped into the sharps disposal container 38, the medical professional releases the downward pressure on the device 10. As a result, the springs 28 decompress, the teeth on the inner surface of the skirt 12 move upward, the gears are rotated in a second direction, the gear portion 34 of the doors are rotated in a first direction, and the doors are rotated upwardly to close the cup 14.

Figure 20:
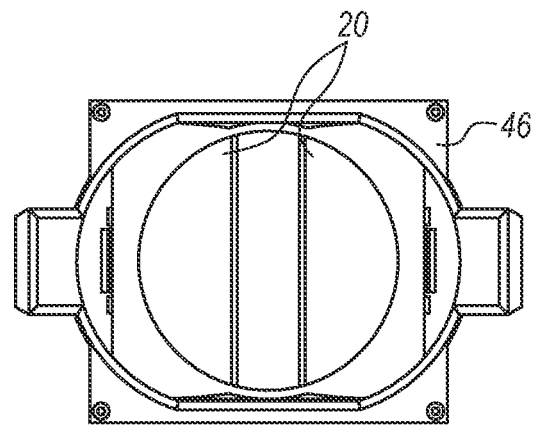
FIG. 20 is a bottom exploded view of the cup and the base of a second preferred embodiment of the needle retention and disposal device.
Figure 21:
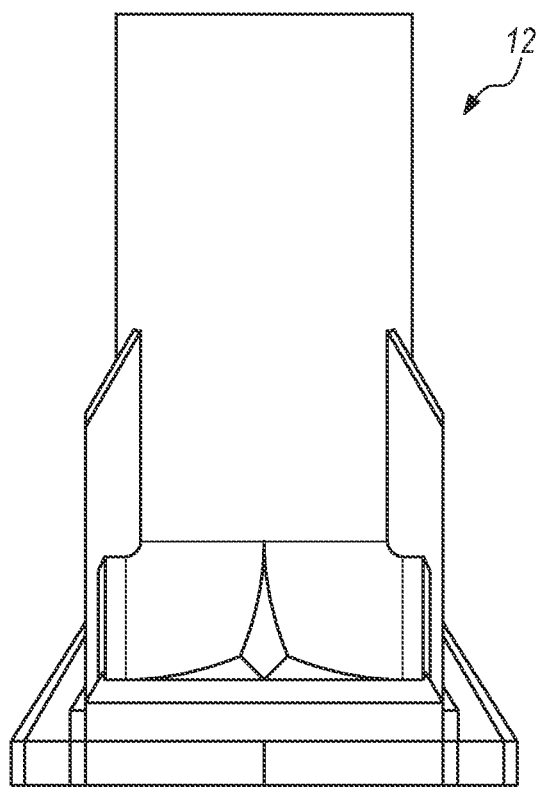
FIG. 21 is a front perspective view of the skirt of a second preferred embodiment of the needle retention and disposal device.
Figure 22:
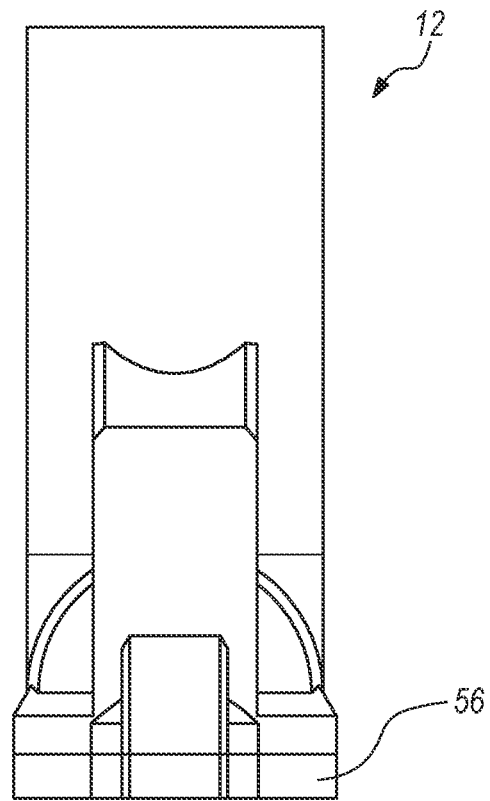
FIG. 22 is a side perspective view of the skirt of a second preferred embodiment of the needle retention and disposal device.
Figure 25:
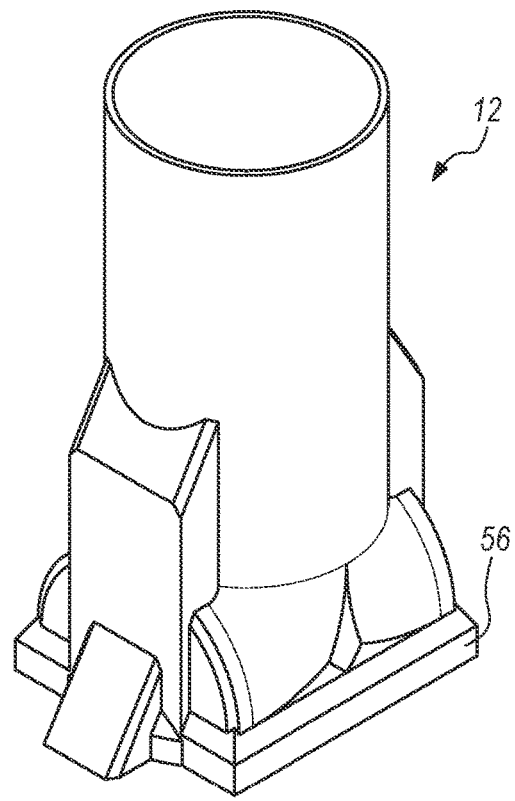
FIG. 25 is a side perspective view of the skirt of a second preferred embodiment of the needle retention and disposal device.

As shown in FIGS. 14-18, the second embodiment of the needle retention and disposal device 10 includes a base 46. The base preferably is fastened to the lower surface of the bottom portion 56 of the skirt 12. In particular, the base 46 shown in FIG. 20 is fastened to the lower surface of the bottom portion 56 of the skirt 12 in the four corners of the base and the skirt using fasteners of the type that would be well-known to those skilled in the art. As shown in FIG. 23, the height of the bottom portion 56 of the skirt may be increased when it is desired for the device 10 to be stably stored on the neck 58 of the sharps container 38 when not in use.

In addition to being used to transport the needles into the patient room, the device may also be used to carry bandages, gauze and other supplies into the patient room. In this regard, the device 10 replaces the tray that is typically used by nurses to carry these medical supplies. For example, in one embodiment, a sleeve is positioned inside the cup 14 and holds the medical supplies. The sleeve preferably includes a lip at the top of the sleeve to aid the medical professional in removing the sleeve from the cup 14 when the supplies are needed.

The present invention has been described with reference to certain preferred and alternative embodiments that are intended to be exemplary only and not limiting to the full scope of the present invention. In this regard, it should be understood that the size and shape of the needle retention and disposal device of the present invention may be changed for more effective use with sharps containers of different types without deviating from the scope of the present invention.

I claim:

1. A needle retention and disposal device comprising:
   a cup having an interior compartment for receiving and retaining a used needle;
   a skirt having a top open end and a bottom open end, wherein said cup is positioned inside said skirt and is springedly attached to said skirt;
   a first door and a second door rotatably attached inside said interior compartment of said cup, wherein said first door and said second door are moveable between an open position and a closed position,
   wherein said bottom open end of said skirt is configured to receive a neck of a sharps container such that said neck of said sharps container contacts a bottom surface of said cup, wherein said first door and said second door are configured to move from said closed position to said open position when said neck of said sharps container contacts said bottom surface of said cup and said skirt is pushed down over said neck of said sharps container.

2. The needle retention and disposal device of claim 1, further comprising a first gear attached to said cup and a second gear attached to said cup.

3. The needle retention and disposal device of claim 2, wherein said first door comprises a first gear portion and said second door comprises a second gear portion.

4. The needle retention and disposal device of claim 3, wherein said first gear is engaged with said first gear portion of said first door and said second gear is engaged with said second gear portion of said second door.

5. The needle retention and disposal device of claim 2, wherein a plurality of teeth line an inner surface of said skirt, wherein at least some of said teeth are engaged with said first gear.

6. The needle retention and disposal device of claim 2, wherein a plurality of teeth line an inner surface of a skirt panel attached to said skirt, wherein at least some of said plurality of teeth are engaged with said first gear.

7. The needle retention and disposal device of claim 1, further comprising a base connected to a lower surface of said skirt.

8. The needle retention and disposal device of claim 7, further comprising weighted material positioned between said base and said skirt.

9. The needle retention and disposal device of claim 1, further comprising a cup retainer, wherein said cup retainer is configured to contact said cup and to prevent downward movement of said cup.

10. The needle retention and disposal device of claim 1, wherein said first door and said second door are configured to move from said open position to said closed position when said skirt is pulled up from said neck of said sharps container.

11. The needle retention and disposal device of claim 1, further comprising a third door and a fourth door.

12. The needle retention and disposal device of claim 1, further comprising a first pin, a second pin, a first compression spring, and a second compression spring, wherein said first pin receives said first compression spring and said second pin receives said second compression spring.

13. The needle retention and disposal device of claim 12, wherein said first pin and said second pin are connected to said cup and said skirt.

* * * * *